United States Patent [19]

Gutschoven et al.

[11] Patent Number: 5,719,281
[45] Date of Patent: Feb. 17, 1998

[54] PREPARATION OF 1/3/5-TRIS(2-HYDROXYALKYL) ISOCYANURATES

[75] Inventors: Frank Gutschoven, Ludwigshafen; Rainer Becker, Bad Dürkheim; Johann-Peter Melder, Neuhofen; Etienne van den Brande; Thomas Krader, both of Kapellen, all of Germany

[73] Assignee: BASF Aktiengesellschaft, Ludwigshafen, Germany

[21] Appl. No.: 621,063

[22] Filed: Mar. 22, 1996

[51] Int. Cl.$^6$ ................................................. C07D 251/34
[52] U.S. Cl. ................................................. 544/221
[58] Field of Search ................................................. 544/221

[56] References Cited

U.S. PATENT DOCUMENTS

| | | | |
|---|---|---|---|
| 3,088,948 | 5/1963 | Little et al. | 260/248 |
| 3,231,577 | 1/1966 | Walles | 260/307 |
| 3,265,694 | 8/1966 | Walles et al. | 260/248 |
| 3,313,812 | 4/1967 | Churchill et al. | 260/248 |

FOREIGN PATENT DOCUMENTS

| | | |
|---|---|---|
| 0 003 620 | 8/1979 | European Pat. Off. . |
| 1 670 214 | 1/1971 | Germany . |
| 16 70 214 | 1/1971 | Germany . |
| 2 124 217 | 12/1971 | Germany . |

OTHER PUBLICATIONS

J. Org. Chem., vol. 28, pp. 85–89, Jan. 1963, Richard W. Cummins, "Reaction Of Cyanuric Acid With Epoxides".
Chemical Abstracts, vol. 71, No. 25, AN–124477w, Dec. 22, 1969, M. Taguchi, et al., "Hydroxyalkyl Isocyanurates".
Chemical Abstracts, vol. 73, No. 3, AN–14878m, Jul. 20, 1970, M. Taguchi, et al., "TRIS(beta–Hydroxyalkyl) Isocyanurates".
Chemical Abstracts, vol. 72, No. 23, AN–121592q, Jun. 8, 1970, A. Saito, et al., "Trishdroxyalkylisocyanurates".

*Primary Examiner*—John M. Ford
*Attorney, Agent, or Firm*—Oblon, Spivak, Mcclellan, Maier & Neustadt, P.C.

[57] ABSTRACT

In a process for preparing 1,3,5-tris(2-hydroxyalkyl) isocyanurates from cyanuric acid and aliphatic epoxides, the reaction is carried out in the presence of catalytic amounts of an organic phosphorus compound.

8 Claims, No Drawings

PREPARATION OF 1/3/5-TRIS(2-HYDROXYALKYL) ISOCYANURATES

The invention relates to a process for preparing 1,3,5-tris(2-hydroxyalkyl) isocyanurates from cyanuric acid and aliphatic epoxides.

It is known that 1,3,5-tris(2-hydroxyalkyl) isocyanurates are generally prepared form cyanuric acid and epoxides (cf. E. Amgwerd, Chemische Rundschau, Volume 23 (1970), No. 45).

In DE-B 1 670 214 it is recommended that this reaction be carried out without catalyst in a lower alcohol or a water-soluble ether as solvent.

Furthermore, it has been proposed that the reaction be carried out in the presence of bases such as alkalies (cf. U.S. Pat. No. 3,088,948) as catalysts.

It is also known that acids such as sulfuric or hydrochloric acid (U.S. Pat. Nos. 3,265,694 and 3,231,577) or alkali metal or alkaline earth metal salts of strong mineral acids (JP-B 1970/15732) can be used as catalyst.

JP-B 1969/23322 describes the use of catalysts such as tertiary amines or derivatives of tertiary amines such as quaternized amines.

However, the above described processes have the disadvantage that the reaction rate is still too slow even at elevated temperature and that high yields are obtained only after a reaction time of some hours. In addition, the thermal stressing of the products and starting materials associated therewith favors secondary reactions. This consequence only really occurs when the reaction temperature is increased further to shorten the cycle time.

It is an object of the present invention to provide a process which makes possible the preparation of 1,3,5-tris(2-hydroxy-alkyl) isocyanurates in high space-time yield at low temperatures, without significant amounts of by-products being formed.

We have found that this object is achieved by a process for preparing 1,3,5-tris(2-hydroxyalkyl) isocyanurates from cyanuric acid and aliphatic epoxides, wherein the reaction is carried out in the presence of catalytic amounts of an organic phosphorus compound.

The process of the present invention is particularly suitable for preparing 1,3,5-tris(2-hydroxyalkyl) isocyanurates of the general formula IV

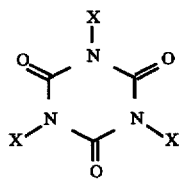  IV where X is a radical of the general formula V

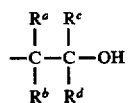  V and $R^a$, $R^b$, $R^c$ and $R^d$ are hydrogen, $C_1$–$C_{10}$-alkyl or $C_5$–$C_8$-cycloalkyl. Valuable intermediates are, in particular, 1,3,5-tris-(2-hydroxyalkyl) isocyanurates in which the radicals $R^a$, $R^b$ and $R^c$ are hydrogen and the radical $R^d$ is $C_1$–$C_{10}$-alkyl or $C_5$–$C_8$-cycloalkyl.

Of particular economic importance are 1,3,5-tris(2-hydroxyethyl) isocyanurate, 1,3,5-tris(2-hydroxypropyl) isocyanurate.

The desired 1,3,5-tris(2-hydroxyalkyl) isocyanurates are prepared by reacting cyanuric acid with the corresponding epoxides.

Suitable aliphatic epoxides are, in particular, those of the general formula I

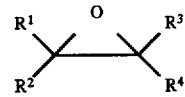  I where $R^1$, $R^2$, $R^3$ and $R^4$ are hydrogen, $C_1$–$C_{10}$-alkyl or $C_5$–$C_8$-cycloalkyl. Particularly useful aliphatic epoxides are inexpensive compounds such as ethylene oxide, propylene oxide, butylene oxide and isobutylene oxide.

In the reaction, it has been found to be useful to use the aliphatic epoxide in a molar excess based on the amount of nitrogen atoms in the cyanuric acid. The molar ratio of aliphatic epoxide to cyanuric acid is therefore at least 3:1, preferably from 3:1 to 3.8:1, particularly preferably from 3.1:1 to 3.6:1.

The reaction is carried out in the presence of organic phosphorus compounds such as phosphoranes, phosphites, phospholidines and particularly favorably using phosphines or aminophosphines.

Suitable phosphines are, for example, those of the general formula II

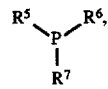  II where $R^5$, $R^6$ and $R^7$ have the following meanings: hydrogen, $C_1$–$C_{20}$-alkyl, in particular $C_1$–$C_6$-alkyl, $C_3$–$C_8$-cycloalkyl, in particular $C_5$- and $C_6$-cycloalkyl, $C_6$–$C_{20}$-aryl, in particular phenyl, $C_5$–$C_{20}$-heteroaryl, $C_7$–$C_{20}$-alkylaryl, in particular tolyl, $C_7$–$C_{20}$-arylalkyl, in particular benzyl, or a radical of the general formula III

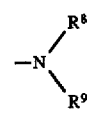  III where $R^8$ and $R^8$ are hydrogen, $C_1$–$C_{20}$-alkyl, in particular $C_1$–$C_6$-alkyl, $C_3$–$C_8$-cycloalkyl, in particular $C_5$- and $C_6$-cycloalkyl, $C_6$–$C_{20}$-aryl, in particular phenyl, $C_5$–$C_{20}$-heteroaryl, $C_7$–$C_{20}$-alkylaryl, in particular tolyl, $C_7$–$C_{20}$-arylalkyl, in particular benzyl.

Among the commercial phosphines, triphenylphosphine, tris(diethylamino)phosphine or tris(dimethylamino) phosphine are particularly suitable.

The organic phosphorus compounds are effective in an amount of only 500 mol-ppm of organic phosphorus compound, based on the cyanuric acid. Use is usually made of up to 50,000 mol-ppm, based on the cyanuric acid. Particularly good results are obtained when they are used in amounts of from 2000 to 10,000 mol-ppm, based on the cyanuric acid.

Advantageously, a tertiary amine, an ammonium salt of a tertiary amine or a quaternary ammonium compound is used in catalytic amounts as cocatalyst in addition to the organic phosphorus compounds.

Suitable amines are those containing one or more tertiary amino groups bearing organic radicals such as $C_1$–$C_{20}$-alkyl, in particular $C_1$–$C_6$-alkyl, $C_3$–$C_8$-cycloalkyl, in particular $C_5$- and $C_6$-cycloalkyl, $C_6$–$C_{20}$-aryl, in particular phenyl, $C_5$–$C_{20}$-heteroaryl, $C_7$–$C_{20}$-alkylaryl, in particular tolyl, $C_7$–$C_{20}$-arylalkyl, in particular benzyl. In the $C_1$–$C_{20}$-alkyl and the $C_3$–$C_8$-cycloalkyl groups, one or 2 of the hydrogen atoms can also be replaced by hydroxyl groups. Among the tertiary amines having a plurality of tertiary andno groups, particularly useful compounds are those in which the nitrogen atoms are connected to one another by units derived from $C_1$-$C_{10}$-hydrocarbon compounds by abstraction of 2 hydrogen atoms, eg. units such as ethylene, propanediyl, butanediyl or phenylene.

Concrete examples of suitable tertiary amines are triethylamine, triethanolamine and 1,4-diazabicyclo[2.2.2] octane.

The tertiary amines can also be used in the form of their ammonium salts. Suitable salts of this type, are, in particular, the adducts of strong organic acids and mineral acids, eg. hydrohalic acids or sulfuric acid, with the tertiary amines.

Suitable organic radicals of the quaternary ammonium compounds are the same ones which are specified as organic radicals of the tertiary amines.

Suitable counter-ions of the quaternary ammonium ions are, apart from the hydroxyl ion, the anions of strong organic acids or mineral acids such as the hydrohalic acids, sulfuric acid and phosphoric acid.

Examples of suitable quaternary ammonium compounds are benzyltrimethylammonium hydroxide, tetrakis(2-hydroxyethyl)ammonium hydroxide or benzyldimethyl-2-hydroxyethylammonium hydroxide.

In general, from 0.05 to 20 mol, preferably from 0.2 to 5 mol, of the cocatalyst is used per mol of organic phosphorus compoud.

The starting materials are generally reacted at from 0° to 180° C. The reaction proceeds well at from 100° to 140° C.; it proceeds particularly well at from 110° to 130° C.

The reaction can be carried out at atmospheric pressure. A pressure higher than atmospheric pressure is advisable when using aliphatic epoxides which are gaseous at the preferred reaction temperatures under atmospheric pressure. When using ethylene oxide and propylene oxide, it is therefore advantageous to employ pressures of from 3 to 20 bar.

The reaction of the starting materials according to the process of the present invention is preferably carried out in the presence of generally customary solvents which react only slowly with the aliphatic epoxides and the cyanuric acid. Preference is given to lower alcohols having from 1 to 6 carbon atoms, in particular propanol and isopropanol, lower ethers having from 2 to 6 carbon atoms, eg. tetrahydrofuran or dioxane, ketones having from 3 to 6 carbon atoms, eg. acetone or butanone, amides such as dimethylformamide or dimethylacetamide.

The solvents are generally used in an amount of from 10 to 1000% by weight, based on the reactants. The amount is advantageously selected so that it is sufficient to dissolve the starting materials at the preferred reaction temperatures.

The process of the present invention is carried out, for example, by metering the aliphatic epoxides into a solution of cyanuric acid, the organic phosphorus compound and, if used, the cocatalyst and a suitable solvent at the temperatures indicated in the ratio described and allowing themixture to react at this temperature until the cyanuric acid has reacted virtually completely to give the 1,3,5-tris(2-hydroxyalkyl) isocyanurate. The conversion reached can be monitored using customary analytical methods (eg. infrared spectroscopy).

The 1,3,5-tris(2-hydroxyalkyl) isocyanurate is isolated using customary methods known to those skilled in the art, eg. by distilling off the solvent and the excess aliphatic epoxides or by crystallizing the 1,3,5-tris(2-hydroxyalkyl) isocyanurate at low temperature and subsequently filtering it off.

In general, reaction times of from 1 to 36 hours, preferably from 3 to 6 hours, are sufficient to obtain the desired 1,3,5-tris-(2-hydroxyalkyl) isocyanurate in high purity and yield.

EXAMPLES 1 TO 5

A reactor was charged with 97 g (0.75 mol) of cyanuric acid, 0.0034 mol of an organic phosphorus compound and, in some cases (Examples 4 and 5), 0.0034 mol of a tertiary amine and 400 ml of n-propanol. At a reaction temperature of 120° C., a total of 51 g (1.2 mol) of ethylene oxide were passed in continuously over a period of 3 hours at a rate which was the same in all experiments.

After the 3 hours had expired, the internal pressure in the reactor was measured and the reactor was subsequently cooled to room temperature. The reaction mixture contained the desired 1,3,5-tris(2-hydroxyethyl) isocyanurate as main product, as well as unreacted ethylene oxide, unreacted cyanuric acid, monohydroxyethyl isocyanurate and dihydroxyethyl isocyanurate.

Since it was ensured that during the reaction the volume of the reactor remained constant and that escape of material from the reactor was impossible, the reaction rate could be determined indirectly by means of the internal pressure in the reactor at the end of the reaction time (3 hours). The higher the internal pressure in the reactor, the lower the conversion of ethylene oxide and, consequently, the lower the reaction rate.

EXAMPLES 6 AND 7 (FOR COMPARISON)

The experiments were carried out using a method similar to that of Examples 1 to 5, but 0.0034 mol of a tertiary amine was used in place of 0.0034 mol of an organic phosphorus compound.

The results of the experiments are shown in Table 1.

TABLE 1

| Example | Catalyst | Internal pressure in the reactor [bar] |
|---|---|---|
| 1 | Triphenylphosphine | 7.9 |
| 2 | Tris(diethylamino)phosphine | 7.7 |
| 3 | Tris(dimethylamino)phosphine | 7.6 |
| 4 | Triphenylphosphine/triethylamine | 7.4 |
| 5 | Triphenylphosphine/triethanolamine | 7.8 |
| 6* | Triethanolamine | 8.5 |
| 7* | Triethylamine | 8.0 |

*for comparison

EXAMPLES 8 TO 11

A reactor was charged with 97 g (0.75 mol) of cyanuric acid, an organic phosphorus compound and, in some cases (Examples 9 and 10), a tertiary amine and 400 ml of n-propanol. At a reaction temperature of 120° C., 17 g (0.39 mol) of ethylene oxide were passed in over a period of 0.5 hours, with the internal pressure in the reactor rising to 8.1 bar. Subsequently, a total of 89 g (2.02 mol) of ethylene oxide were injected at the specified temperature, this being carried out so as to keep the pressure constant at 8.1 bar. The time necessary for this further amount of ethylene oxide to be injected is a measure of the reaction rate and is shown, along with other process parameters, in Table 2.

The amounts of phosphorus compound and amino compound used were 0.0034 mol of each in the Examples 8, 9 and 11. In Example 10, the corresponding amounts were 0.0017 mol.

EXAMPLE 11 (FOR COMPARISON)

Example 8 was repeated, but 0.52 g (0.0034 mol) of triethanolamine was used in place of triphenylphosphine.

TABLE 2

| Example | Catalyst | Further injection time [h] | Yield[1] [%] |
|---|---|---|---|
| 8 | Triphenylphosphine | 2.6 | 89 |
| 9 | Triphenylphosphine/ triethylamine | 3.25 | 88 |
| 10 | Triphenylphosphine/ triethylamine | 4.1 | — |
| 11* | Triethanolamine | 5.6 | 87 |

*for comparison
[1] of tris(hydroxyethyl) isocyanurate

EXAMPLE 12

A reactor was charged with 97 g (0.75 mol) of cyanuric acid, 0.55 g (0.0034 mol) of tris(dimethylamino)phosphine and 400 ml of dimethylformamide. Subsequently, sufficient nitrogen was injected for the internal pressure to be 3 bar at room temperature. The reaction mixture was then heated to 120° C. At this temperature, a total of 51 g (1.2 mol) of ethylene oxide were injected over a period of 3 hours at a constant metering rate. The internal pressure was 0.5 bar after 3 hours. The level of the internal pressure is a measure of the reaction rate, with higher pressure indicating a lower conversion of ethylene oxide and thus a lower reaction rate.

EXAMPLE 13

Example 12 was repeated, but using 0.19 g (0.0034 mol) of KOH (potassium hydroxide) as catalyst. The internal pressure after passing in ethylene oxide for 3 hours was 0.7 bar.

EXAMPLE 14

A reactor was charged with 97 g (0.75 mol) of cyanuric acid, 900 mg of triphenylphosphine and 400 ml of n-propanol. At a reaction temperature of 120° C., a total of 107 g (1.8 mol) of propylene oxide were passed in over a period of 17 hours. Subsequently, the reaction was stopped by means of cooling, the reactor was vented and the reaction product was analyzed. At least one propylene oxide unit had been added to 99.8 mol % of the cyanuric acid.

We claim:

1. A process for preparing a 1,3,5-tris-(2-hydroxyalkyl) isocyanurate, which comprises:

reacting an aliphatic epoxide of the formula (I):

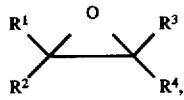

wherein $R^1$, $R^2$, $R^3$ and $R^4$ are each independently hydrogen, $C_1$–$C_{10}$ alkyl or $C_5$–$C_8$ cycloalkyl;

with cyanuric acid in the presence of an organic phosphine compound as a catalyst having the formula (II):

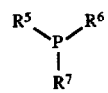

wherein $R^5$, $R^6$ and $R^7$ are each independently hydrogen, $C_1$–$C_{20}$ alkyl, $C_3$–$C_8$-cycloalkyl, $C_6$–$C_{20}$-aryl, $C_5$–$C_{20}$-heteroaryl, $C_7$–$C_{20}$-alkylaryl, $C_7$–$C_{20}$-arylalkyl or a radical of the formula (III):

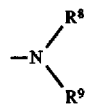

wherein $R^8$ and $R^9$ are each independently hydrogen, $C_1$–$C_{20}$-alkyl, $C_3$–$C_8$-cycloalkyl, $C_6$–$C_{20}$-aryl, $C_5$–$C_{20}$-heteroaryl, $C_7$–$C_{20}$-alkylaryl or $C_7$–$C_{20}$-arylalkyl.

2. The process of claim 1, wherein said phosphine is used in the amount of from 500 to 50,000 mol-ppm based on the amount of cyanuric acid used.

3. The process of claim 1, wherein the reaction is carried out at from 100° to 140° C.

4. The process of claim 1, wherein said phosphine is selected from the group consisting of triphenylphosphene, tris(dimethylamino)phosphine and tris(dimethylamino) phosphine.

5. The process of claim 1, which further comprises effecting said reaction in the presence of a catalytic amount of a co-catalyst selected from the group consisting of tertiary amines, ammonium salts of tertiary amines and quaternary ammonium compounds.

6. The process of claim 5, wherein said co-catalyst is selected from the group consisting of triethylamine, 1,4-diazabicyclo(2.2.2)octane, benzyltrimethylammonium hydroxide, tetrakis(2-hydroxyethyl)ammonium hydroxide, triethanolamine and benzyldemethyl-2-hydroxyethylammonium hydroxide.

7. The process of claim 5, wherein from 0.05 to 20 mol of the co-catalyst is used per mol of the phosphine compound.

8. The process of claim 1, wherein said reaction is carried out in a solution of propanol or dimethylformamide.

* * * * *

UNITED STATES PATENT AND TRADEMARK OFFICE
CERTIFICATE OF CORRECTION

PATENT NO. : 5,719,281
DATED : February 17, 1998
INVENTOR(S) : Frank GUTSCHOVEN et al.

It is certified that error appears in the above-identified patent and that said Letters Patent is hereby corrected as shown below:

On the title page, insert item [30]:

[30] Foreign Application Priority Data

Mar. 22, 1995 [DE] Germany............19510325.4

On the title page, item [54] and column 1, lines 1-2, the title should read:-- PREPARATION OF 1,3,5-TRIS(2-HYDROXYALKYL) ISOCYANURATES--

Signed and Sealed this

Twelfth Day of May, 1998

Attest:

BRUCE LEHMAN

Attesting Officer　　Commissioner of Patents and Trademarks